US00PP29411P3

(12) United States Plant Patent
Klemm et al.

(10) Patent No.: US PP29,411 P3
(45) Date of Patent: Jun. 19, 2018

(54) ***PELARGONIUM* PLANT NAMED 'KLEPP16381'**

(50) Latin Name: *Pelargonium peltatum*
Varietal Denomination: KLEPP16381

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days. days.

(21) Appl. No.: 15/731,356

(22) Filed: Jun. 1, 2017

(65) Prior Publication Data

US 2017/0367239 P1 Dec. 21, 2017

(30) Foreign Application Priority Data

Jun. 16, 2016 (CH) ..... PBR 16-3073

(51) Int. Cl.
*A01H 5/02* (2018.01)

(52) U.S. Cl.
USPC ..... Plt./332
CPC ..... *A01H 5/0277* (2013.01)

(58) Field of Classification Search
USPC ..... Plt./332
CPC ..... A01H 5/0277
See application file for complete search history.

*Primary Examiner* — Kent L Bell
(74) *Attorney, Agent, or Firm* — Bethany R. Roahrig; Barbara Campbell; Cochran Freund & Young LLC

(57) ABSTRACT

A new *pelargonium* plant particularly distinguished by purple red colored flowers and a hanging growth habit, is disclosed.

1 Drawing Sheet

Genus and species: *Pelargonium peltatum.*
Variety denomination: 'KLEPP16381'.

CROSS REFERENCE TO RELATED APPLICATION

The present application claims priority to Switzerland Plant Variety Protection Application No. 16-3073, as filed on Jun. 16, 2016, the entire contents are herein incorporated by reference for all the application teaches and discloses.

BACKGROUND OF THE NEW PLANT

The present invention comprises a new and distinct variety of *pelargonium*, botanically known as *Pelargonium peltatum* and hereinafter referred to by the variety name 'KLEPP16381'. 'KLEPP16381' originated from a cross-combination in July 2010 in Stuttgart, Germany between the female *pelargonium* variety 'PP-2008-0688' (unpatented) and the proprietary male *pelargonium* variety 'PP-2006-0064' (unpatented).

Seeds from the cross-combination were obtained and sown and plants were grown for evaluation. A single plant was selected in June 2011 and subsequently named 'KLEPP16381'. In August 2011 'KLEPP16381' was first vegetatively propagated in Stuttgart, Germany by vegetative cuttings from branches. 'KLEPP16381' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Purple red flowers; and
2. A hanging growth habit.

DESCRIPTION OF THE PHOTOGRAPH

This new *pelargonium* plant is illustrated by the accompanying photograph which shows an overall view of the plant. The photograph is of an approximately five to six months old plant grown in Stuttgart, Germany under greenhouse conditions in September 2013. The colors shown are as true as can be reasonably obtained by conventional photographic procedures.

DESCRIPTION OF THE NEW VARIETY

The following detailed descriptions set forth the distinctive characteristics of 'KLEPP16381'. The data which define these characteristics were collected from asexual reproductions carried out in Stuttgart, Germany. Data was collected on plants grown four months after planting in Stuttgart, Germany under a glass covered greenhouse in May 2017. Color references are to The R.H.S. Colour Chart of The Royal Horticultural Society of London (R.H.S.), 5$^{th}$ edition (2007).

Classification:
*Family.*—Geraniaceae.
*Botanical.*—*Pelargonium peltatum.*
*Common.*—*Pelargonium.*
*Designation.*—'KLEPP16381'.

Parentage:
*Female parent.*—The proprietary *pelargonium* variety 'PP-2008-0688' (unpatented).
*Male parent.*—The proprietary *pelargonium* variety 'PP-2006-0064' (unpatented).

Plant:
*Form.*—Bushy and round.
*Habit.*—Hanging.
*Height.*—15.0 cm.
*Spread.*—20.0 cm.
*Natural flowering season.*—Spring to autumn.
*Propagation type.*—Vegetative cuttings.
*Time to produce a finished flowering plant.*—3 months.
*Time to initiate and develop roots.*—21 days.
*Root description.*—White and fine.

Stems:
*Quantity of stems per plant.*—4 to 5.
*Color.*—RHS 137B.
*Surface texture.*—Smooth.
*Stem form.*—Round.
*Diameter.*—0.5 cm.
*Length.*—8.0 cm.
*Internode length.*—2.0 cm to 4.0 cm.
*Anthocyanin.*—Absent.

Leaves:
*Arrangement.*—Alternate.
*Shape.*—Ivy-shaped.
*Apex.*—Obtuse.
*Base.*—Obtuse.
*Margin.*—Entire and lobed.
*Texture* (*both surfaces*).—Smooth.
*Length.*—8.0 cm.
*Width.*—8.0 cm.
*Color.*—Upper surface: RHS 137A and RHS 187A. Lower surface: RHS 137B.
*Petiole.*—Length: 4.0 cm to 7.0 cm. Diameter: 0.2 cm. Color: RHS 138B. Strength: Medium.
*Venation pattern.*—Palmate.
*Venation color.*—Upper surface: RHS 137B. Lower surface: RHS 137D.

Inflorescence:
*Lastingness of flowers on the plant.*—8 to 10 days.
*Umbels.*—Quantity of umbels per plant: 3 to 5. Length: 8.0 cm. Diameter: 8.0 cm.
*Individual florets of the umbel.*—Quantity of florets per umbel: 6 to 10. Depth: 2.0 cm. Diameter: 5.5 cm.
*Fragrance.*—Absent.

Flower buds:
*Cluster shape.*—Round.
*Cluster size.*—Length: 3.0 cm. Width: 3.0 cm.
*Surface texture.*—Moderately pubescent.
*Bud.*—Height: 1.0 cm. Width: 0.6 cm. Shape: Elliptic. Apex: Acute. Base: Obtuse. Margin: Entire. Color: RHS 137C.

Petals:
*Quantity per flower.*—10 to 12.
*Shape.*—Obtriangular.
*Apex.*—Round.
*Base.*—Obtuse.
*Margin.*—Entire.
*Length.*—3.0 cm.
*Width.*—1.8 cm.
*Texture* (*both surfaces*).—Smooth.
*Color of lobes.*—Upper lobes: Upper surface: RHS 53A. Lower surface: RHS 58B. Lower lobes: Upper surface: RHS 53A. Lower surface: RHS 58B.

Petaloids:
*Quantity per flower.*—1 to 5.
*Shape.*—Moderate.
*Apex.*—Moderate.
*Base.*—Obtuse.
*Margin.*—Entire.
*Length.*—0.5 cm to 2.0 cm.
*Width.*—0.3 cm to 0.8 cm.
*Texture* (*both surfaces*).—Smooth.
*Color.*—Upper surface: RHS 53A. Lower surface: RHS 53B.

Sepals:
*Number per flower.*—5.
*Shape.*—Elliptic.
*Apex.*—Acute.
*Base.*—Obtuse.
*Margin.*—Entire.
*Surface texture.*—Upper surface: Smooth. Lower surface: Moderately pubescent.
*Color.*—Upper surface: RHS 137B. Lower surface: RHS 176C and RHS 138B.
*Length.*—1.8 cm.
*Width.*—0.7 cm.

Pedicel:
*Length.*—3.0 cm.
*Diameter.*—0.15 cm.
*Color.*—RHS 176C and RHS 138B.
*Surface texture.*—Sparsely pubescent.
*Strength.*—Medium.

Peduncle:
*Length.*—10.0 cm to 12.0 cm.
*Diameter.*—0.4 cm.
*Color.*—RHS 137C.
*Surface texture.*—Smooth.
*Strength.*—Medium to strong.

Reproductive organs:
*Stamens.*—Quantity of stamens per flower: 5. Anther length: 0.2 cm. Filament length: 0.7 cm. Filament color: RHS 65D. Pollen amount: Moderate. Pollen color: RHS 31B.
*Pistils.*—Number: 1. Stigma color: RHS 60D. Style length: 0.3 cm. Style color: RHS 65C. Ovary arrangement: Central. Ovary color: RHS 138D. Ovary diameter: 0.1 cm. Ovary length: 0.5 cm.

Fruit and seed set: None observed.

Disease and pest/insect resistance: None observed.

COMPARISON WITH PARENTAL LINES AND KNOWN VARIETY

'KLEPP16381' is distinguished from its parents as described in Table 1:

TABLE 1

Comparison with Parental Lines

| Characteristic | 'KLEPP16381' | Female parent 'PP-2008-0688' | Male Parent 'PP-2006-0064' |
|---|---|---|---|
| Growth | Medium | Medium | Strong |
| Earliness | Medium | Very early | Medium |
| Flower color | Purple red | Orange red | Orange red |

'KLEPP16381' can be compared to the commercial variety 'KLEPP12267', also known as 'Royal Night' (unpatented). Differences between the two varieties are described in Table 2:

TABLE 2

| Comparison with Similar Variety | | |
|---|---|---|
| Characteristic | 'KLEPP16381' | Commercial line 'KLEPP12267' |
| Flower color | Purple red | Deep purple red |
| Growth | Medium | Compact |

We claim:

1. A new and distinct variety of *pelargonium* plant named 'KLEPP16381' as illustrated and described herein.

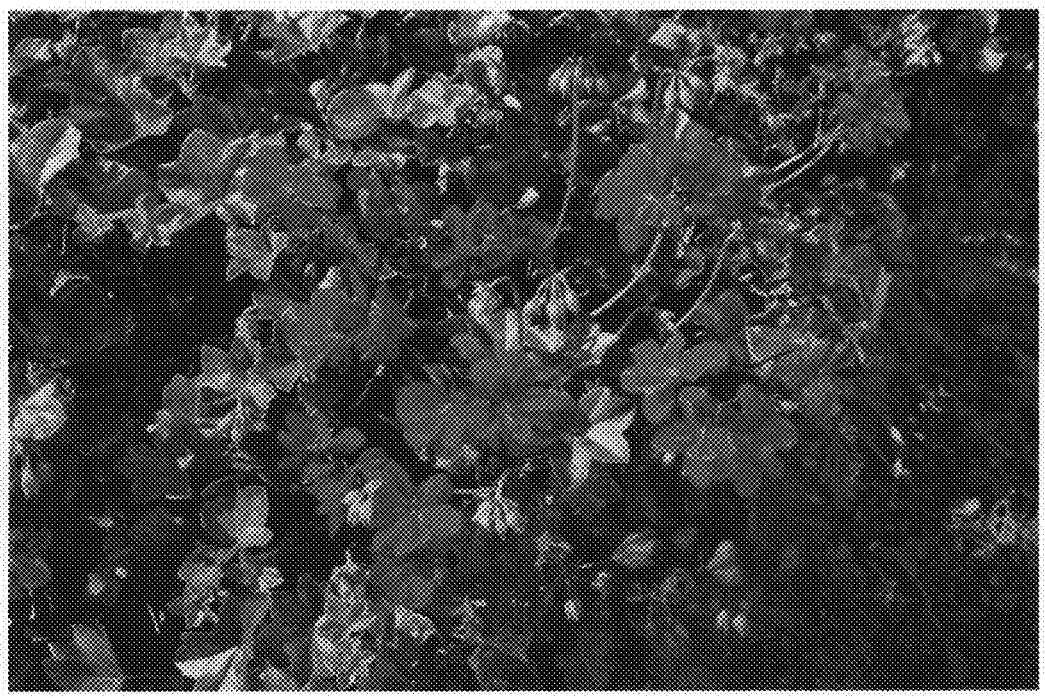

* * * * *